(12) United States Patent
Vainer et al.

(10) Patent No.: US 9,488,922 B2
(45) Date of Patent: Nov. 8, 2016

(54) METHODS AND APPARATUS FOR INSPECTION OF ARTICLES, EUV LITHOGRAPHY RETICLES, LITHOGRAPHY APPARATUS AND METHOD OF MANUFACTURING DEVICES

(75) Inventors: Yuri Vainer, Troitsk (RU); Vadim Yevgenyevich Banine, Deurne (NL); Luigi Scaccabarozzi, Valkenswaard (NL); Arie Jeffrey Den Boef, Waalre (NL)

(73) Assignee: ASML Netherlands B.V., Veldhoven (NL)

( * ) Notice: Subject to any disclaimer, the term of this patent is extended or adjusted under 35 U.S.C. 154(b) by 348 days.

(21) Appl. No.: 13/883,083

(22) PCT Filed: Oct. 6, 2011

(86) PCT No.: PCT/EP2011/067491
§ 371 (c)(1),
(2), (4) Date: Aug. 14, 2013

(87) PCT Pub. No.: WO2012/076216
PCT Pub. Date: Jun. 14, 2012

(65) Prior Publication Data
US 2014/0146297 A1 May 29, 2014

Related U.S. Application Data

(60) Provisional application No. 61/420,075, filed on Dec. 6, 2010.

(51) Int. Cl.
*G01J 1/42* (2006.01)
*G03F 7/20* (2006.01)
(Continued)

(52) U.S. Cl.
CPC ............. *G03F 7/7085* (2013.01); *G01N 21/94* (2013.01); *G01N 21/956* (2013.01); *G01N 21/95623* (2013.01); *G03F 1/84* (2013.01); *G01N 2021/95676* (2013.01); *G03F 1/24* (2013.01)

(58) Field of Classification Search
USPC .................. 356/237.1–237.6, 239.3–239.8
See application file for complete search history.

(56) References Cited

U.S. PATENT DOCUMENTS 6,407,810 B1 * 6/2002 Liu et al. ................ 356/237.4
7,304,310 B1 12/2007 Shortt et al.
(Continued)

FOREIGN PATENT DOCUMENTS

| EP | 1 452 851 A1 | 9/2004 |
| JP | 11-304717 A | 11/1999 |

(Continued)

OTHER PUBLICATIONS

English-Language Abstract for Japanese Patent Publication No. 11-304717 A, published Nov. 5, 1999; 1 page.
(Continued)

*Primary Examiner* — Tri T Ton
(74) *Attorney, Agent, or Firm* — Sterne, Kessler, Goldstein & Fox P.L.L.C.

(57) ABSTRACT

An EUV lithography reticle is inspected to detect contaminant particles. The inspection apparatus comprises illumination optics with primary radiation. An imaging optical system with plural branches is arranged to form and detect a plurality of images, each branch having an image sensor and forming its image with a different portion of radiation received from the illuminated article. A processor combines information from the detected images to report on the presence and location of contaminant particles. In one or more branches the primary radiation is filtered out, so that the detected image is formed using only secondary radiation emitted by contaminant material in response to the primary radiation. In a dark field imaging branch using the scattered primary radiation, a spatial filter blocks spatial frequency components associated with periodic features of the article under inspection, to allow detection of particles which cannot be detected by secondary radiation.

20 Claims, 7 Drawing Sheets

(51) Int. Cl.
*G01N 21/94* (2006.01)
*G01N 21/956* (2006.01)
*G03F 1/84* (2012.01)
*G03F 1/24* (2012.01)

(56) References Cited

U.S. PATENT DOCUMENTS

| | | |
|---|---|---|
| 2004/0001196 A1* | 1/2004 | Shibazaki et al. ............ 356/129 |
| 2007/0258086 A1 | 11/2007 | Bleeker et al. |
| 2009/0303450 A1 | 12/2009 | Hintersteiner |
| 2010/0149505 A1 | 6/2010 | Sewell et al. |
| 2012/0182538 A1 | 7/2012 | Koole et al. |

FOREIGN PATENT DOCUMENTS

| | | |
|---|---|---|
| JP | 2007-258567 A | 10/2007 |
| JP | 2010-145993 A | 7/2010 |
| WO | WO 2004/008125 A1 | 1/2004 |
| WO | WO 2011/015412 A1 | 2/2011 |

OTHER PUBLICATIONS

English-Language Abstract for Japanese Patent Publication No. 2007-258567 A, published Oct. 4, 2007; 1 page.

International Search Report directed to related International Patent Application No. PCT/EP2011/067491, mailed Feb. 2, 2012; 3 pages.

International Preliminary Report on Patentability and Written Opinion of the International Searching Authority directed to related International Patent Application No. PCT/EP2011/067491, issued Jun. 12, 2013; 6 pages.

* cited by examiner (a)　　　(b)　　　(c)

METHODS AND APPARATUS FOR INSPECTION OF ARTICLES, EUV LITHOGRAPHY RETICLES, LITHOGRAPHY APPARATUS AND METHOD OF MANUFACTURING DEVICES

CROSS-REFERENCE TO RELATED APPLICATIONS

This application claims the benefit of U.S. provisional application 61/420,075, which was filed on 6 Dec. 2010, and which is incorporated herein in its entirety by reference.

FIELD

The invention relates to inspection of articles, and may be applied for example to inspection of patterned articles in the field of lithography. In that example, the article to be inspected can for example be a reticle or other patterning device. The invention has been developed particularly for inspection of reticles used in EUV lithography, but is not limited to such application. The invention provides methods and apparatuses for use in inspection, lithographic apparatus, and reticles adapted for inspection by such methods.

BACKGROUND

Lithography is widely recognized as one of the key steps in the manufacture of integrated circuits (ICs) and other devices and/or structures. However, as the dimensions of features made using lithography become smaller, lithography is becoming a more critical factor for enabling miniature IC or other devices and/or structures to be manufactured.

The lithographic apparatus of is a machine that applies a desired pattern onto a substrate, usually onto a target portion of the substrate. The lithographic apparatus of can be used, for example, in the manufacture of ICs. In that instance, a patterning device, which is alternatively referred to as a mask or a reticle, may be used to generate a circuit pattern to be formed on an individual layer of the IC. This pattern can be transferred onto a target portion (e.g., including part of, one, or several dies) on a substrate (e.g., a silicon wafer). Transfer of the pattern is typically via imaging onto a layer of radiation-sensitive material (resist) provided on the substrate. In general, a single substrate will contain a network of adjacent target portions that are successively patterned.

Current lithography systems project mask pattern features that are extremely small. Dust or extraneous particulate matter appearing on the surface of the reticle can adversely affect the resulting product. Any particulate matter that deposits on the reticle before or during a lithographic process is likely to distort features in the pattern being projected onto a substrate. Therefore, the smaller the feature size, the smaller the size of particles critical to eliminate from the reticle.

A pellicle is often used with a reticle. A pellicle is a thin transparent layer that may be stretched over a frame above the surface of a reticle. Pellicles are used to block particles from reaching the patterned side of a reticle surface. Although particles on the pellicle surface are out of the focal plane and should not form an image on the wafer being exposed, it is still preferable to keep the pellicle surfaces as particle-free as possible.

A theoretical estimate of the limits of pattern printing can be given by the Rayleigh criterion for resolution as shown in equation (1):

$$CD = k_1 * \frac{\lambda}{NA_{PS}} \tag{1}$$

where $\lambda$ is the wavelength of the radiation used, NAPS is the numerical aperture of the projection system used to print the pattern, k1 is a process dependent adjustment factor, also called the Rayleigh constant, and CD is the feature size (or critical dimension) of the printed feature. It follows from equation (1) that reduction of the minimum printable size of features can be obtained in three ways: by shortening the exposure wavelength $\lambda$, by increasing the numerical aperture NAPS or by decreasing the value of k1.

In order to shorten the exposure wavelength and, thus, reduce the minimum printable size, it has been proposed to use an extreme ultraviolet (EUV) radiation source. EUV radiation sources are typically configured to output a radiation wavelengths of around 5-20 nm, for example, 13.5 nm or about 13 nm. Thus, EUV radiation sources may constitute a significant step toward achieving small features printing. Such radiation is termed extreme ultraviolet or soft x-ray, and possible sources include, for example, laser-produced plasma sources, discharge plasma sources, or synchrotron radiation from electron storage rings.

For EUV lithography processes, however, pellicles are not used, because they would attenuate the imaging radiation. When reticles are not covered, they are prone to particle contamination, which may cause defects in a lithographic process. Particles on EUV reticles are one of the main sources of imaging defects. An EUV reticle (or other reticle for which no pellicle is employed) is likely to be subjected to organic and inorganic particle contamination. Particle sizes as small as around 20 nm could lead to fatal defects on the wafer and to zero yield.

Inspection and cleaning of an EUV reticle before moving the reticle to an exposure position can be an important aspect of a reticle handling process. Reticles are typically cleaned when contamination is suspected, as a result of inspection, or on the basis of historical statistics. Cleaning usually shortens the reticle lifetime, so unnecessary cleaning is to be avoided.

Reticles are typically inspected with optical techniques. However, a pattern scatters light exactly in the same way as a particle does. The pattern of a reticle surface can be arbitrary (i.e., non-periodic), and so there is no way to distinguish a particle from the pattern by simply analyzing the scattered light. A reference is always required with these optical techniques, either die-to-die, or die-to-database. Moreover, existing inspection tools are expensive and relatively slow.

SUMMARY

An object inspection system is provided that can operate at high speed and that can detect particles of small size, for example of a size of 100 nm or less, 50 nm or less, or 20 nm or less. A technique is also provided that can detect particles that are present on the patterned side of a patterning device, such as a reticle, used in an EUV lithographic apparatus.

According to a first aspect of this disclosure, there is provided a method for inspection of an article, for example an lithography reticle, to detect contaminant particles, the method comprising: illuminating at least a portion of the article with primary radiation at one or more first wavelengths, forming and detecting an image of the illuminated article with an imaging optical system comprising detection optics and an image sensor, and filtering out the first wavelength(s) of radiation in the imaging optical system, so that the detected image is formed using only radiation at one or more second wavelengths different from the first wavelengths, thereby to obtain an image showing the presence and location of contaminant particles using secondary radiation emitted by material of the contaminant particles in response to the primary radiation.

The invention in the first aspect further provides an inspection apparatus for inspecting an article to detect and locate contaminant particles the apparatus comprising: a radiation source for generating primary radiation at one or more first wavelengths, illumination optics arranged to receive the primary radiation and to illuminate at least a portion of the article with the primary radiation, an imaging optical system comprising detection optics arranged to form an image of the illuminated article and an image sensor arranged to detect the image, and a filter arranged within the imaging optical system to remove the first wavelength(s) of radiation, so that the detected image is formed using only radiation at one or more second wavelengths different from the first wavelengths, thereby to obtain an image showing the presence and location of contaminant particles using secondary radiation emitted by material of the contaminant particles in response to the primary radiation.

Optionally, the imaging optical system comprises a plurality of branches operating in parallel, each branch forming and detecting an image using radiation of a different wavelength or wavelengths selected by filters from the secondary radiation while filtering out the primary radiation.

Optionally, at least a portion of the filtered out primary radiation is diverted into a dark field imaging system having a spatial filter in an intermediate pupil plane, thereby to form and detect a dark field image of the article under inspection. In one embodiment the spatial filter is a programmable spatial light modulator operable to block different spatial frequency components when inspecting different articles.

The invention in a second aspect provides a method for inspection of an article to detect contaminant particles, the method comprising: illuminating the article with primary radiation at one or more first wavelengths, forming and detecting a plurality of images of the illuminated article using respective branches of an imaging optical system each having an image sensor and forming its image with a different portion of radiation received from the illuminated article, and combining information from two or more of the detected images to report on the presence and location of contaminant particles.

In embodiments of this aspect, the plurality of images may be formed using different portions of the secondary radiation, and/or one or more images may be formed with different portions of the primary radiation, for example in a dark field imaging branch.

The invention further provides The lithographic apparatus of, for example an EUV lithographic apparatus, comprising a support for a patterning device, a support for a substrate and a projection optical system for transferring a pattern from the patterning device to the substrate, the lithographic apparatus further comprising an inspection apparatus according to the invention of either aspect as set forth above, operable to inspect the patterning device without removing the patterning device from the lithographic apparatus.

The invention yet further provides a method of manufacturing a device, wherein a patterning device is inspected for contaminant particles by a method of inspection according to either aspect of the invention as set forth above, wherein depending on the result of the inspection the patterning device is cleaned or not cleaned, and wherein the patterning device is used to apply a device pattern to a device substrate in The lithographic apparatus of, for example an EUV lithographic apparatus.

Further features and advantages of the invention, as well as the structure and operation of various embodiments of the invention, are described in detail below with reference to the accompanying drawings. It is noted that the invention is not limited to the specific embodiments described herein. Such embodiments are presented herein for illustrative purposes only. Additional embodiments will be apparent to persons skilled in the relevant art(s) based on the teachings contained herein.

BRIEF DESCRIPTION OF THE DRAWINGS/FIGURES

The accompanying drawings, which are incorporated herein and form part of the specification, illustrate the present invention and, together with the description, further serve to explain the principles of the invention and to enable a person skilled in the relevant art(s) to make and use the invention. Embodiments of the invention are described, by way of example only, with reference to the accompanying drawings.

Figure 1:
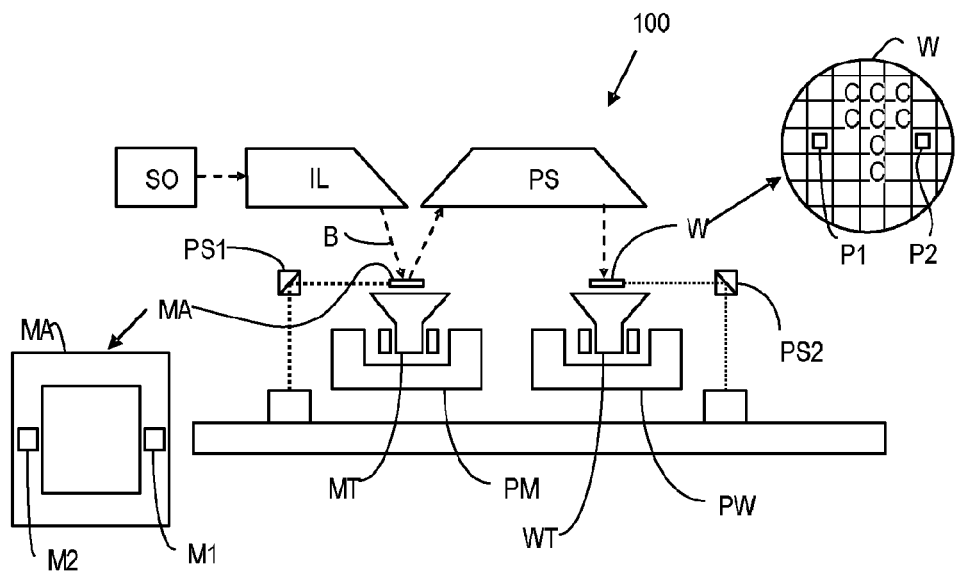
FIG. 1 depicts schematically the lithographic apparatus of having reflective projection optics.

The features and advantages of the present invention will become more apparent from the detailed description set forth below when taken in conjunction with the drawings, in which like reference characters identify corresponding elements throughout. In the drawings, like reference numbers generally indicate identical, functionally similar, and/or structurally similar elements.

DETAILED DESCRIPTION

This specification discloses one or more embodiments that incorporate the features of this invention. The disclosed embodiment(s) merely exemplify the invention. The scope of the invention is not limited to the disclosed embodiment(s). The invention is defined by the claims appended hereto.

The embodiment(s) described, and references in the specification to "one embodiment", "an embodiment", "an example embodiment", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is understood that it is within the knowledge of one skilled in the art to effect such feature, structure, or characteristic in connection with other embodiments whether or not explicitly described.

Embodiments of the invention may be implemented in hardware, firmware, software, or any combination thereof. Embodiments of the invention may also be implemented as instructions stored on a machine-readable medium, which may be read and executed by one or more processors. A machine-readable medium may include any mechanism for storing or transmitting information in a form readable by a machine (e.g., a computing device). For example, a machine-readable medium may include read only memory (ROM); random access memory (RAM); magnetic disk storage media; optical storage media; flash memory devices; electrical, optical, acoustical or other forms of propagated signals (e.g., carrier waves, infrared signals, digital signals, etc.), and others. Further, firmware, software, routines, instructions may be described herein as performing certain actions. However, it should be appreciated that such descriptions are merely for convenience and that such actions in fact result from computing devices, processors, controllers, or other devices executing the firmware, software, routines, instructions, etc.

Before describing such embodiments in more detail, however, it is instructive to present an example environment in which embodiments of the present invention may be implemented.

FIG. 1 schematically depicts the lithographic apparatus of 100 including a source collector module SO according to one embodiment of the invention. The apparatus comprises an illumination system (illuminator) IL configured to condition a radiation beam B (e.g., EUV radiation), a support structure (e.g., a mask table) MT constructed to support a patterning device (e.g., a mask or a reticle) MA and connected to a first positioner PM configured to accurately position the patterning device, a substrate table (e.g., a wafer table) WT constructed to hold a substrate (e.g., a resist-coated wafer) W and connected to a second positioner PW configured to accurately position the substrate, and a projection system (e.g., a reflective projection system) PS configured to project a pattern imparted to the radiation beam B by patterning device MA onto a target portion C (e.g., comprising one or more dies) of the substrate W.

The illumination system may include various types of optical components, such as refractive, reflective, magnetic, electromagnetic, electrostatic or other types of optical components, or any combination thereof, for directing, shaping, or controlling radiation.

The support structure MT holds the patterning device MA in a manner that depends on the orientation of the patterning device, the design of the lithographic apparatus, and other conditions, such as for example whether or not the patterning device is held in a vacuum environment. The support structure can use mechanical, vacuum, electrostatic or other clamping techniques to hold the patterning device. The support structure may be a frame or a table, for example, which may be fixed or movable as required. The support structure may ensure that the patterning device is at a desired position, for example with respect to the projection system.

The term "patterning device" should be broadly interpreted as referring to any device that can be used to impart a radiation beam with a pattern in its cross-section such as to create a pattern in a target portion of the substrate. The pattern imparted to the radiation beam may correspond to a particular functional layer in a device being created in the target portion, such as an integrated circuit.

The patterning device may be transmissive or reflective. Examples of patterning devices include masks, programmable mirror arrays, and programmable LCD panels. Masks are well known in lithography, and include mask types such as binary, alternating phase-shift, and attenuated phase-shift, as well as various hybrid mask types. An example of a programmable mirror array employs a matrix arrangement of small mirrors, each of which can be individually tilted so as to reflect an incoming radiation beam in different directions. The tilted mirrors impart a pattern in a radiation beam which is reflected by the mirror matrix.

The projection system, like the illumination system, may include various types of optical components, such as refractive, reflective, magnetic, electromagnetic, electrostatic or other types of optical components, or any combination thereof, as appropriate for the exposure radiation being used, or for other factors such as the use of a vacuum. It may be desired to use a vacuum for EUV radiation since other gases may absorb too much radiation. A vacuum environment may therefore be provided to the whole beam path with the aid of a vacuum wall and vacuum pumps.

As here depicted, the apparatus is of a reflective type (e.g., employing a reflective mask).

The lithographic apparatus may be of a type having two (dual stage) or more substrate tables (and/or two or more mask tables). In such "multiple stage" machines the additional tables may be used in parallel, or preparatory steps may be carried out on one or more tables while one or more other tables are being used for exposure.

Referring to FIG. 1, the illuminator IL receives an extreme ultra violet radiation beam from the source collector module SO. Methods to produce EUV light include, but are not necessarily limited to, converting a material into a plasma state that has at least one element, e.g., xenon, lithium or tin, with one or more emission lines in the EUV range. In one such method, often termed laser produced plasma ("LPP") the required plasma can be produced by irradiating a fuel, such as a droplet, stream or cluster of material having the required line-emitting element, with a laser beam. The source collector module SO may be part of an EUV radiation system including a laser, not shown in FIG. 1, for providing the laser beam exciting the fuel. The resulting plasma emits output radiation, e.g., EUV radiation, which is collected using a radiation collector, disposed in the source collector module. The laser and the source collector module may be separate entities, for example when a $CO_2$ laser is used to provide the laser beam for fuel excitation.

In such cases, the laser is not considered to form part of the lithographic apparatus and the radiation beam is passed from the laser to the source collector module with the aid of a beam delivery system comprising, for example, suitable directing mirrors and/or a beam expander. In other cases the source may be an integral part of the source collector module, for example when the source is a discharge produced plasma EUV generator, often termed as a DPP source.

The illuminator IL may comprise an adjuster for adjusting the angular intensity distribution of the radiation beam. Generally, at least the outer and/or inner radial extent (commonly referred to as σ-outer and σ-inner, respectively) of the intensity distribution in a pupil plane of the illuminator can be adjusted. In addition, the illuminator IL may comprise various other components, such as facetted field and pupil mirror devices. The illuminator may be used to condition the radiation beam, to have a desired uniformity and intensity distribution in its cross-section.

The radiation beam B is incident on the patterning device (e.g., mask) MA, which is held on the support structure (e.g., mask table) MT, and is patterned by the patterning device. After being reflected from the patterning device (e.g., mask) MA, the radiation beam B passes through the projection system PS, which focuses the beam onto a target portion C of the substrate W. With the aid of the second positioner PW and position sensor PS2 (e.g., an interferometric device, linear encoder or capacitive sensor), the substrate table WT can be moved accurately, e.g., so as to position different target portions C in the path of the radiation beam B. Similarly, the first positioner PM and another position sensor PS1 can be used to accurately position the patterning device (e.g., mask) MA with respect to the path of the radiation beam B. Patterning device (e.g., mask) MA and substrate W may be aligned using mask alignment marks M1, M2 and substrate alignment marks P1, P2.

The depicted apparatus could be used in at least one of the following modes:
1. In step mode, the support structure (e.g., mask table) MT and the substrate table WT are kept essentially stationary, while an entire pattern imparted to the radiation beam is projected onto a target portion C at one time (i.e., a single static exposure). The substrate table WT is then shifted in the X and/or Y direction so that a different target portion C can be exposed.
2. In scan mode, the support structure (e.g., mask table) MT and the substrate table WT are scanned synchronously while a pattern imparted to the radiation beam is projected onto a target portion C (i.e., a single dynamic exposure). The velocity and direction of the substrate table WT relative to the support structure (e.g., mask table) MT may be determined by the (de-)magnification and image reversal characteristics of the projection system PS.
3. In another mode, the support structure (e.g., mask table) MT is kept essentially stationary holding a programmable patterning device, and the substrate table WT is moved or scanned while a pattern imparted to the radiation beam is projected onto a target portion C. In this mode, generally a pulsed radiation source is employed and the programmable patterning device is updated as required after each movement of the substrate table WT or in between successive radiation pulses during a scan. This mode of operation can be readily applied to maskless lithography that utilizes programmable patterning device, such as a programmable mirror array of a type as referred to above.

Combinations and/or variations on the above described modes of use or entirely different modes of use may also be employed.

Figure 2:
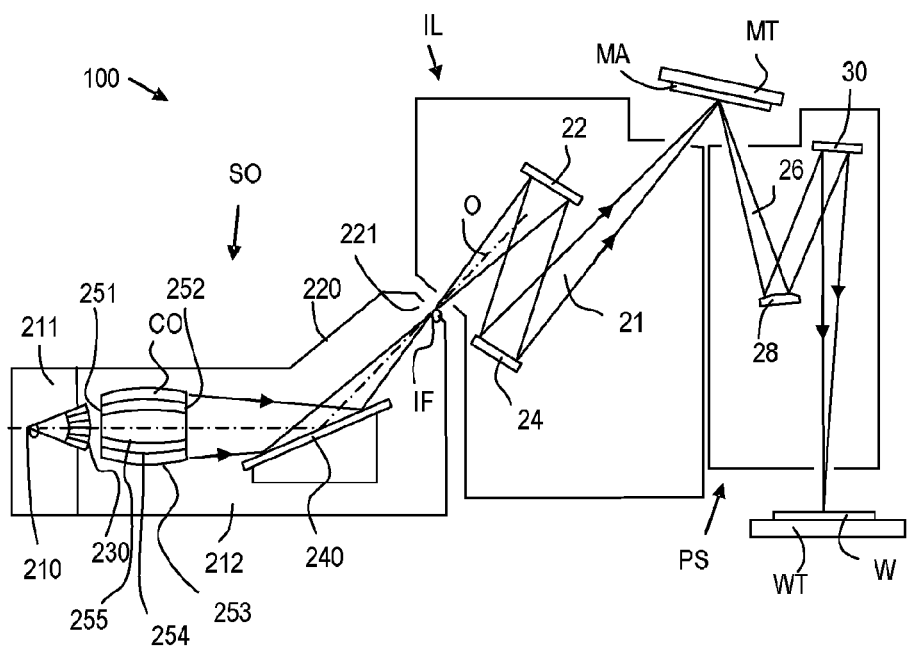
FIG. 2 is a more detailed view of the apparatus of FIG. 1.

FIG. 2 shows the apparatus 100 in more detail, including the source collector module SO, the illumination system IL, and the projection system PS. The source collector module SO is constructed and arranged such that a vacuum environment can be maintained in an enclosing structure 220 of the source collector module SO. An EUV radiation emitting plasma 210 may be formed by a discharge produced plasma source. EUV radiation may be produced by a gas or vapor, for example Xe gas, Li vapor or Sn vapor in which the very hot plasma 210 is created to emit radiation in the EUV range of the electromagnetic spectrum. The very hot plasma 210 is created by, for example, an electrical discharge causing an at least partially ionized plasma. Partial pressures of, for example, 10 Pa of Xe, Li, Sn vapor or any other suitable gas or vapor may be required for efficient generation of the radiation. In an embodiment, a plasma of excited tin (Sn) is provided to produce EUV radiation.

The radiation emitted by the hot plasma 210 is passed from a source chamber 211 into a collector chamber 212 via an optional gas barrier or contaminant trap 230 (in some cases also referred to as contaminant barrier or foil trap) which is positioned in or behind an opening in source chamber 211. The contaminant trap 230 may include a channel structure. Contamination trap 230 may also include a gas barrier or a combination of a gas barrier and a channel structure. The contaminant trap or contaminant barrier 230 further indicated herein at least includes a channel structure, as known in the art.

The collector chamber 211 may include a radiation collector CO which may be a so-called grazing incidence collector. Radiation collector CO has an upstream radiation collector side 251 and a downstream radiation collector side 252. Radiation that traverses collector CO can be reflected off a grating spectral filter 240 to be focused in a virtual source point IF. The virtual source point IF is commonly referred to as the intermediate focus, and the source collector module is arranged such that the intermediate focus IF is located at or near an opening 221 in the enclosing structure 220. The virtual source point IF is an image of the radiation emitting plasma 210.

Subsequently the radiation traverses the illumination system IL, which may include a facetted field mirror device 22 and a facetted pupil mirror device 24 arranged to provide a desired angular distribution of the radiation beam 21, at the patterning device MA, as well as a desired uniformity of radiation intensity at the patterning device MA. Upon reflection of the beam of radiation 21 at the patterning device MA, held by the support structure MT, a patterned beam 26 is formed and the patterned beam 26 is imaged by the projection system PS via reflective elements 28, 30 onto a substrate W held by the wafer stage or substrate table WT.

More elements than shown may generally be present in illumination optics unit IL and projection system PS. The grating spectral filter 240 may optionally be present, depending upon the type of lithographic apparatus. Further, there may be more mirrors present than those shown in the Figures, for example there may be 1-6 additional reflective elements present in the projection system PS than shown in FIG. 2.

Collector optic CO, as illustrated in FIG. 2, is depicted as a nested collector with grazing incidence reflectors 253, 254 and 255, just as an example of a collector (or collector mirror). The grazing incidence reflectors 253, 254 and 255 are disposed axially symmetric around an optical axis O and a collector optic CO of this type is preferably used in combination with a discharge produced plasma source, often called a DPP source.

Figure 3:
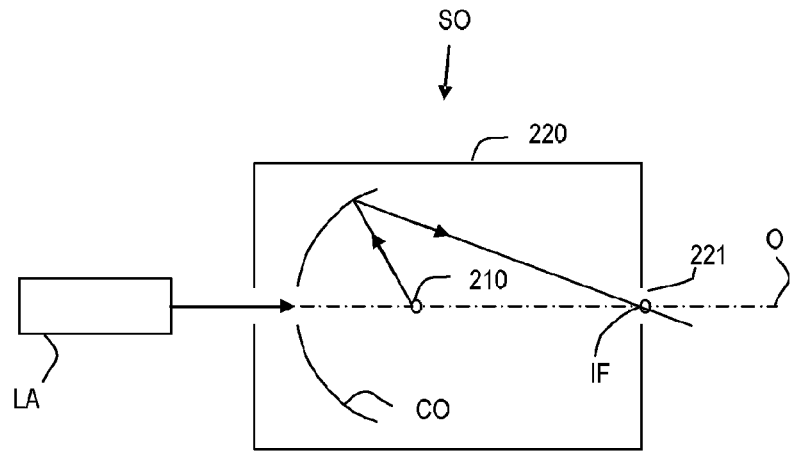
FIG. 3 is a more detailed view of an alternative source collector module SO for the apparatus of FIGS. 1 and 2.

Alternatively, the source collector module SO may be part of an LPP radiation system as shown in FIG. 3. A laser LA is arranged to deposit laser energy into a fuel, such as xenon (Xe), tin (Sn) or lithium (Li), creating the highly ionized plasma 210 with electron temperatures of several 10's of eV. The energetic radiation generated during de-excitation and recombination of these ions is emitted from the plasma, collected by a near normal incidence collector optic CO and focused onto the opening 221 in the enclosing structure 220.

Figure 4:
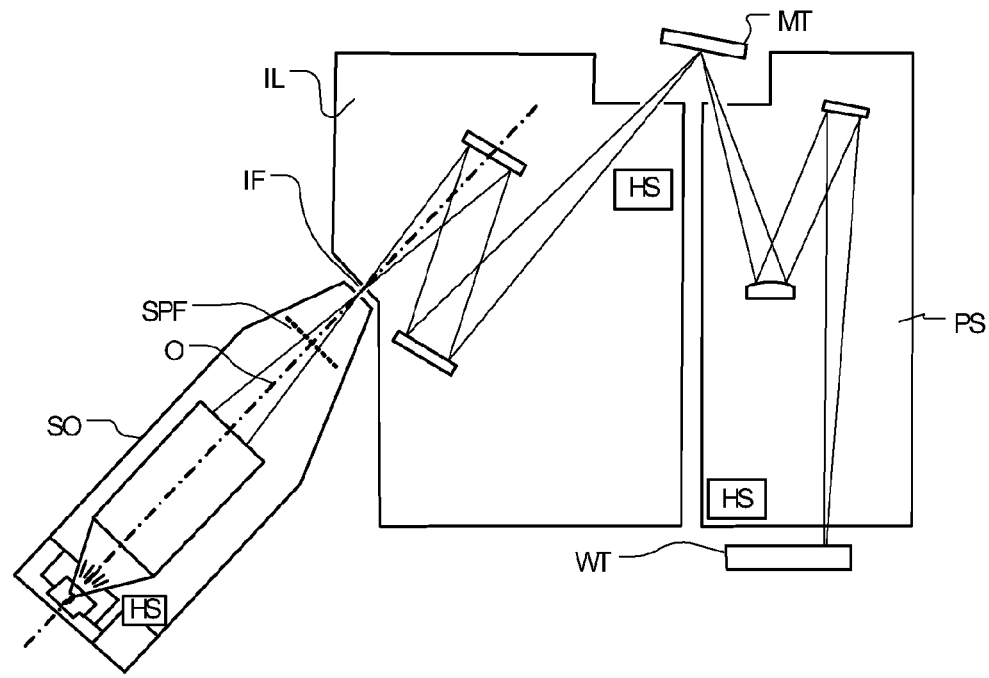
FIG. 4 depicts an alternative example of an EUV lithographic apparatus.

FIG. 4 shows an alternative arrangement for an EUV lithographic apparatus in which the spectral purity filter SPF is of a transmissive type, rather than a reflective grating. The radiation from source collector module SO in this case follows a straight path from the collector to the intermediate focus IF (virtual source point). In alternative embodiments, not shown, the spectral purity filter 11 may be positioned at the virtual source point 12 or at any point between the collector 10 and the virtual source point 12. The filter can be placed at other locations in the radiation path, for example downstream of the virtual source point 12. Multiple filters can be deployed. As in the previous examples, the collector CO may be of the grazing incidence type (FIG. 2) or of the direct reflector type (FIG. 3).

It has been proposed to use the presence or absence of a photoluminescence (PL) signal as an indicator of the presence of a defect on a semiconductor substrate, see for example JP 2007/258567 or JP 11-304717, which are incorporated by reference herein in their entireties. However, improvements to the particle detection capabilities of these techniques would be welcomed. A spectroscopic approach to detection of contaminants on an EUV lithography reticle has been proposed in international patent application PCT/EP2010/059460 which was filed on 2 Jul. 2010 and claims priority from U.S. provisional application 61/231,161, filed on 4 Aug. 2009, which are incorporated by reference herein in their entireties. In particular, time-resolved spectroscopy is described. In order to determine the actual position of contaminant particles on the reticle, a search process is proposed in which the area inspected is made smaller and smaller. This requires several measurement steps and adds greatly to the time required for inspection. In our U.S. provisional patent application 61/369,916, which was filed on 2 Aug. 2010, it is suggested to add fluorescent marker dyes that will bind preferentially to the contaminants, to allow detection of contamination with greater sensitivity, which is incorporated by reference herein in its entirety. US 20090303450 A discloses an inspection method in which a liquid crystal (LC) device is used as an adaptive filter to remove the pattern of a reticle, so that an image showing the approximate location of a contaminant particle can be obtained, which is incorporated by reference herein in its entirety.

The following description presents systems and methods of object inspection that allow the detection of particles on the object. The object to be inspected can be, for example, a lithographic patterning device for generating a circuit pattern to be formed on an individual layer in an integrated circuit. Example patterning devices include a mask, a reticle, or a dynamic patterning device. Reticles for which the system can be used include for example reticles with periodic patterns and reticles with non-periodic patterns. The reticles can also be for use within any lithography process, such as EUV lithography and imprint lithography for example.

Figure 5:
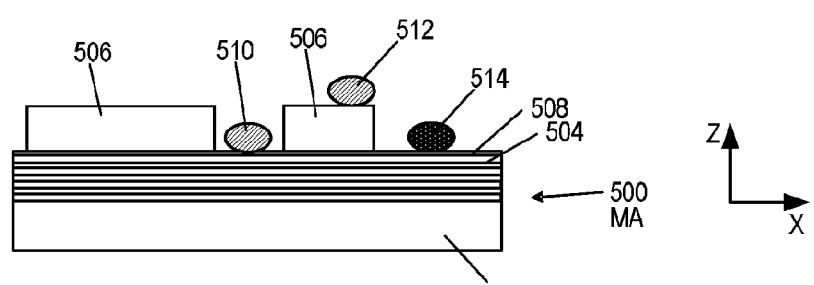
FIG. 5 depicts an EUV reticle with contaminant particles.

FIG. 5 illustrates a typical EUV reticle 500 in cross section, which may be the patterning device MA in any of the lithographic apparatuses of FIGS. 1 to 4. Reticle 500 comprises a substrate 502, multilayer coating 504 and pattern layer 506.

In one example embodiment the reticle 500 can be a EUV reticle including a substrate 502 formed from quartz or another low thermal expansion material, and a reflective multilayer coating 504 including alternate molybdenum and silicon layers. The multilayer coating 504 may for example include several tens of layers and can in one example have a thickness of about 200 nm. A capping layer 508 can also be provided at the top surface of the multilayer, being formed for example from ruthenium or silicon.

The pattern layer 506 defines a pattern for the reticle 500. In the case of an EUV reticle the pattern layer 506 is an absorber layer. Similarly, the multilayer 504 in an EUV reticle is reflective.

The pattern layer 506 in an EUV reticle can for example be formed from tantalum nitride (TaN). There may be a surface layer of TaNO. The height of the absorber may in one example be approximately 70 nanometers, and it can have a width of approximately 100 nm (which is approximately four times the critical dimension (CD) of the lithography system, the scaling being due to the demagnification factor between wafer and reticle).

The pattern defined by the pattern layer is in principle arbitrary and can be composed of lines, contact holes, periodic and non periodic patterns. In certain embodiments of the invention, described further below, the presence of periodic patterns in certain areas of the reticle is exploited to permit the detection of some contaminant particles. However, a technique is sought which will detect contaminant independently of the pattern.

The diagram also shows contaminant particles 510, 512 and 514. These are not part of the reticle 500 but may be adsorbed or deposited on the reticle 500 in some situations. Because a lithography apparatus is complicated and utilizes many different materials, any type of particle can in principle be deposited on the reticle 500. The particles can be conductive or insulating, they can be of any shape or size and could be deposited on the conductive coating 504 or the pattern layer 506. Example types of particle that might be deposited include organic particles, metal particles and metal oxide particles.

When electromagnetic radiation is incident on a surface of a solid, secondary radiation of photons occurs in addition to the regular reflection of the radiation. There are many processes for generation of secondary photon radiation on the surfaces of solids. Three ones which are of interest in the present field of application are: photoluminescence (PL), inelastic light scattering processes (such as Raman scattering, and surface enhanced Raman scattering (SERS)), and elastic light scattering. Other processes such as non-linear generation may be useful in other applications. The efficiency of each of these phenomena depends on the type of material involved. Particles which gather on a surface of a patterning device such as a reticle used in The lithographic apparatus of will in general be of a different type of material from those materials from which the patterning device is formed. In the examples which follow (FIGS. 6 to 11), this fact is exploited to aid in the detection of contaminant particles by exploiting one or more types of photoluminescence exhibited by at least some of the types of contaminant particle. The inventors have used photoluminescence and Raman spectroscopy techniques to analyze the different responses of different materials. More details of these experiments are presented, with example spectra, in the earlier PCT application PCT/EP2010/059460, which is incorporated by reference herein in its entirety. This information is incorporated herein by reference, as background for understanding the present invention.

First Embodiment

Figure 6:
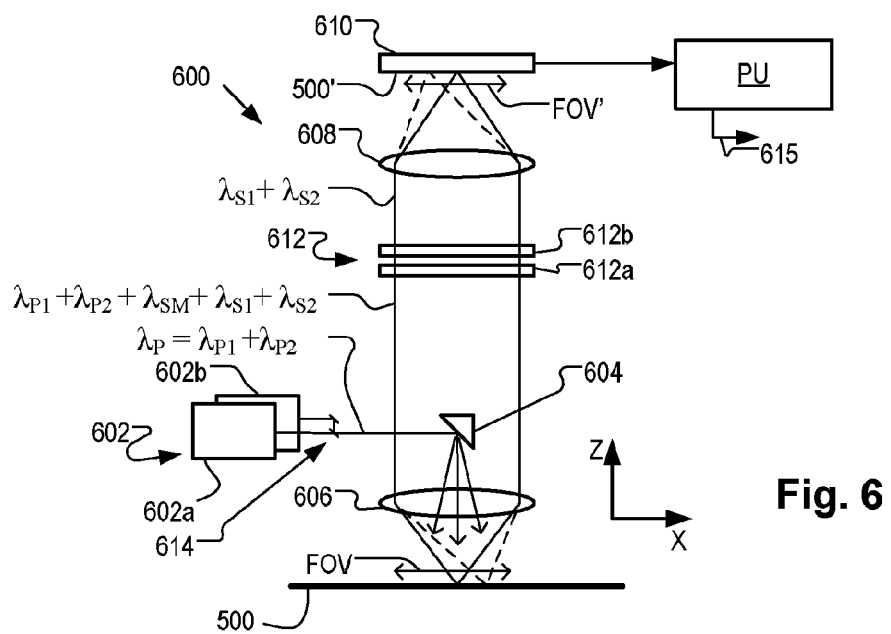
FIG. 6 depicts schematically an apparatus for inspection of an object according to a first embodiment of the present invention and illustrates principles of operation of an inspection process for EUV reticles.

FIG. 6 illustrates the principles of the particle detection methods disclosed herein. An inspection apparatus 600 according to a first embodiment of the invention is provided which includes a radiation source 602 which illuminates reticle 500 via illumination optics which in this example includes one or more mirrors 604 which illuminates a field of view FOV of the inspection apparatus with radiation directed from a desired range of angles. Source 602 provides one or more types of primary radiation at a wavelength λP which is selected to be a suitable excitation wavelength for photoluminescence in one or more types of contaminant particles. In practice, the primary radiation may comprise several wavelengths which we can label λP1, λP2 etc. Contaminant particles are brought into an excited state by this illumination after which they can emit secondary radiation at a different wavelength λS by one or more photoluminescence mechanisms. It may be desired in practice to use two or more different wavelengths of secondary radiation to improve detection of contaminant particles. These different wavelengths, which we can label λS1, λS2 etc., may be wavelengths emitted by different types of contamination material, or by different photoluminescence processes within the same material. Detection optics including objective lens 606 and imaging lens 608 collect the emitted radiation and deliver it to sensor 610, which in this case is a camera sensor having a 2-dimensional array of pixels sensitive to the secondary radiation wavelength. Images formed by radiation falling on sensor 610 are converted to pixel data and processed in a processing unit PU. The field of view FOV of the instrument is imaged to an image field FOV' on the sensor 610. In this schematic diagram, no magnification is shown, but in a real system the image field could be larger or smaller than the field of view FOV. Magnification is likely in practice. A large collection area on the sensor will keep the incident power density small. Throughput will normally be greatest with an optical system having a large etendue, depending heavily on the detector area.

As described in the prior applications, mentioned above, shadowing effects caused by the height of the pattern layer 506 can make it difficult to illuminate particles which are nestled between portions of the absorber material forming pattern layer 506. As in the prior application, illumination may be directed at the reticle 500 from directly above, to avoid shadowing. Alternatively or in addition, radiation can be directed at the reticle obliquely, but from a range of angles so that no part of the reticle surface is completely shadowed. The radiation from source 602 may pass through objective lens 606 which is part of detection optics, or it may travel completely independently. The illumination optics may comprise reflective and/or transmissive elements. The disclosure of different forms of illumination optics in the prior application PCT/EP2010/059460 is hereby incorporated by reference in its entirety.

The radiation received by objective lens 606 will include a relatively large amount of scattered primary radiation and the secondary radiation emitted by contaminants, if any are present, represents a very much weaker signal. A filter 612 is therefore provided within the detection optics, which is designed to block the primary radiation wavelength(s) λP while passing the secondary radiation wavelength(s) λS. In the prior application mentioned above, imaging of the reticle surface was not performed. Rather, scattered and emitted radiation from all parts of the reticle, within a field of view of the instrument, are integrated into a single optical signal, which is delivered via an optical fiber to a spectrometer. The spectrometer analyzes the received radiation in the energy (wavelength or frequency) domain to obtain a spectrum. The major signal comprising radiation simply scattered by the reticle pattern can be easily subtracted from the observed spectrum, as it has the same spectrum as the illumination. Secondary radiation emitted by the material of the reticle itself can also be predicted and well characterized in advance. The secondary radiation emitted by the reticle is labeled with a wavelength λSM in the diagrams. As with any of the wavelength components labeled in the diagram, this may actually be a collection of wavelengths attributable to the material or materials of the reticle, and the label λSM is used as shorthand for this collection of wavelengths. After subtracting these components λSM and λP from the observed signal in a processing unit similar to unit PU of the present apparatus, any residual signal that remains is assumed to belong to a foreign material, which is to a particle.

The apparatus of FIG. 6 and the embodiments to be described further below overcome certain limitations of the apparatus described in the prior application. One limitation of the spectrographic approach is that all radiation from a relatively large area (in this context, perhaps 1 mm2) is integrated into a single signal, so that the location of a contaminant particle is not resolved within the area size. Multiple scans of sub-areas can be performed, as described in the prior application, but this increases the inspection time Another drawback in the practical embodiment of the spectrographic apparatus is that a detector employed in the spectrograph is typically a CCD (charge-coupled device) image sensor having a 2-dimensional array of pixels, of which only one axis is used to resolve the spectrum. In the other dimension of the sensor, the signals of all pixels are integrated together to obtain the value of the spectrum at a single wavelength of frequency. At the same time, however, the dark current of those pixels is also integrated. This increases the noise per unit wavelength of the instrument, and hence decreases the sensitivity to contaminant signals. Also, with spatial resolution, data interpretation is much easier: in fact particle radiation is very localized, so it immediately clear whether we are seeing a particle or some artifacts which are usually not localized but present for all spatial coordinates.

A further limitation of the apparatus described in the prior application arises generally from the small etendue of the spectrograph, which is typically characterized by a numerical aperture (NA) in the region of 0.13 or smaller, and with an usable entrance aperture of approximately 2×6 mm2. Although higher etendue spectrographs exist, they usually suffer from other limitations. Avoiding these drawbacks, the inspection apparatus of FIG. 6 and the following additional embodiments does not acquire a spectrum and perform filtering in software, but rather applies filtering in the optical domain using the filter 612. The inventors have recognized that in practice the spectral regions to be filtered out (principally the primary radiation wavelengths) can be sufficiently narrow that they can be separated using band filters along a beam path of the imaging optics, without the need to separate the signal into a spectrum. Accordingly, the need for a spectrograph is avoided and the apparatus simply images the reticle on a standard CCD or similar image sensor in two-dimensions. In this way, the apparatus significantly increases the acquisition etendue, and consequently allows an increasing sensitivity and/or decrease in the inspection time. If source 602 generates radiation at wavelengths that are not wanted as primary radiation for the inspection of the reticle using photoluminescence, these unwanted wavelengths can optionally be filtered out at the source, and not in the detection optics. The different primary radiation wavelengths λP1, λP2 etc. may however be wanted to increase the emission of secondary radiation by a particular type of contaminant, or to provoke secondary emission by different materials, and thereby to allow more types of contaminant particle to be detected by the apparatus.

Figure 8:
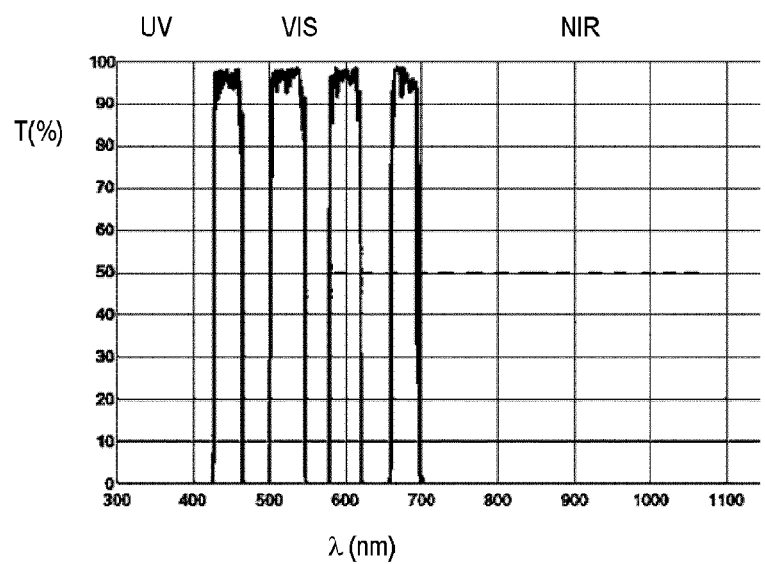
FIG. 8 shows a transmission spectrum of a commercially-available multi-pass optical filter usable in embodiments of the invention.

The design of filter 612 may be simplified by making it from a combination of more than one element 612a, 612b, each defining a particular notch frequency or pass band. Since a portion of the wanted radiation will generally be lost at filter interfaces, in general it will be desired to use as few elements as possible. A multi-band filter response is illustrated in FIG. 8 and described further below. At the same time, the range of wavelengths to be passed and detected by the imaging sensor 610 may be very wide indeed, perhaps ranging from ultraviolet (UV) to infrared in making the design of the optical system very challenging. Therefore cost and/or performance of the imaging optics may be undesirable in such cases. Some modifications and measures that can be deployed to increase design freedom in these circumstances will be described further below.

Figure 7:
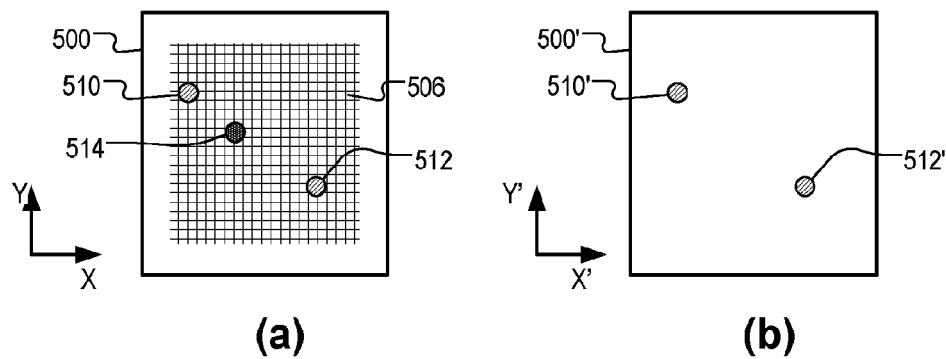
FIG. 7 illustrates (a) the spatial distribution of contaminant particles on an EUV reticle and (b) a corresponding contaminant image obtained using the apparatus of FIG. 6.

FIG. 7(a) is a plan view of the reticle 500 under inspection by the apparatus of FIG. 6. As mentioned already, the field of view of the apparatus may be somewhat smaller than the entire reticle surface, so that multiple images must be obtained, to perform a complete inspection. For simplicity of the present illustration, FIG. 7 is presented as if the entire reticle can be imaged in one go. In practice, the field of view FOV of the inspection apparatus may be a small portion of the reticle area, and a series of images will be taken at stepped intervals to cover the entire area of interest. These images can be processed independently or they can be stitched into a larger image, as desired. Instead of stepping, fast acquisition can be done by "scanning" using so-called time delay and integration or TDI techniques. TDI is a known technique for imaging moving subjects using special synchronization of readout and movement of a CCD-based camera. Although faster, TDI may bring a penalty in sensitivity, so it is a matter of experiment and design choice, which technique will be used.

In FIG. 7(b), 500' represents the image of the reticle area, as formed on and detected by image sensor 610 in the inspection apparatus. Axes X' and Y' on the image sensor correspond to the real axes x and y on the reticle. The pattern features formed by pattern layer 506 on the reticle are represented by hatching in FIG. 7(a). Because the scattered primary radiation and secondary radiation emitted by the reticle materials are blocked by filter 612, the pattern features do not contribute to the image of the reticle shown in FIG. 7(b). On the other hand, because contaminant particles 510 and 512 respond to the primary radiation by emitting secondary radiation at wavelengths which are not blocked by filter 612, images 510' and 512' of these particles appear prominently enough within the sensor image of FIG. 7(b) that they may be detected by processing unit PU.

Note that another type of contaminant particle, labeled 514 does not appear in the image 500' and so is not detected by the apparatus in this simple embodiment. Because of the filter design, a contaminant particle which is of the same or similar material as the reticle itself will of course not be detected in this example. In order to allow the detection of more types of particle such as particle 514, different situations may be considered. In the first type of situation, particle 514 is of a different material to the reticle that does not emit secondary radiation in sufficient quantity to be detected, under the same conditions as particles 510 and 512 are detected. Knowing the different types of material that are typically found as contaminants and are to be detected, source 602 may in practice comprise several individual laser sources 602a and 602b, whose radiation is combined optically at 614 to provide the primary wavelength components $\lambda P1$, $\lambda P2$ etc. It may be desired to image the reticle using two or more different wavelengths $\lambda S1$, $\lambda S2$ etc. of secondary radiation to improve detection of contaminant particles. These different wavelengths, may be wavelengths emitted by different types of contamination, or wavelengths emitted by the same contamination in response to different wavelength components in the primary radiation. In that case, imaging at different wavelengths $\lambda S1$, $\lambda S2$ allows more types of contaminant particle to be detected. The different wavelengths of secondary radiation may be emitted by different photoluminescence mechanisms within the same type of contaminant particle, possibly in response to different wavelengths of primary radiation. In that case, imaging using different wavelengths $\lambda S1$, $\lambda S2$ allows contaminant particles to be detected with greater certainty. Filter 612 in the embodiment of FIG. 6 should therefore pass all the wanted wavelengths $\lambda S1$, $\lambda S2$ etc. of secondary radiation. The design of filter 612 may again be simplified by making it from a combination of more than one elements 612a, 612b. Since radiation will be lost at filter interfaces, in general it will be desired to use as few elements as possible.

Processing unit PU has an output 615 for delivering an inspection result to an operator, or to an automatic control system of the lithographic apparatus. In embodiments where unit PU is physically the same as the control unit of the larger apparatus, the result may of course be delivered internally. The result may be delivered on a dedicated hardware output, or as a message on multi-purpose communication channel. The inspection result indicates at least the presence and location of suspected contamination. It may optionally provide more detailed parameters of what is detected, for example intensity information.

FIG. 8 shows the performance in transmission T against wavelength for a commercially-available multi-notch filter. The horizontal access runs in wavelength from 300 nm in the ultraviolet (UV) part of the spectrum, through the visible range (VIS) and into the (near) infrared (NIR), up to a wavelength of 1100 nm at the right hand side. Within each pass band, it will be seen that the transmittance T is in excess of 90%, while outside the pass bands, transmittance falls very steeply virtually to zero. Filters having these characteristics are available from a number of suppliers. The characteristic illustrated in FIG. 8 relates to a filter manufactured and offered by the company Semrock, Rochester, N.Y. 14624 USA (www.semrock.com). Filters are available from this company having single or multiple pass bands, single or multiple notches and so forth. Filters are available specifically to support Raman spectroscopy.

The use of filters having multiple passing and/or blocking bands in a single filter helps to reduce the loss of useful radiation at interfaces. The fact that the filter 612 is deployed in a part of the imaging optical system in which the rays of radiation are parallel helps to ensure a consistent filter response across all rays. To realize the benefits mentioned above in a practical embodiment, one can assume firstly that the response of the reticle materials is very well known, so that the contribution $\lambda SM$ can be subtracted reliably by filter 612. Also, it helps if the secondary radiation from the reticle (or other substrate being inspected) is limited to a relatively narrow band in the electro-magnetic spectrum. Otherwise, at least some of the secondary radiation of the reticle cannot be easily subtracted and it will essentially add to the baseline noise, thus decreasing the sensitivity of the inspection process. From preliminary experiments, this condition seems to be verified for typical EUV reticles, and can be tested also for other types of product that may be inspected.

Filters can be custom designed with a very precise multi-layer structure to provide, the desired response. The commercially-available filter used as an example in FIG. 8 has four very distinct pass bands which are visible in the graph at around 440 nm, 520 nm, 600 nm and 680 nm. For the present application, it is likely that a custom filter will be needed. In an example of the present invention discussed further below, we might specify a multi)-notch filter to stop the excitation wavelengths 266, 355, 532 nm, which are the 4th, 3rd and 2nd harmonic of a YAG laser. If there is significant secondary radiation contribution from the reticle materials, stop/pass-band and/or edge filters can be provided.

Unlike the spectrograph embodiments, the etendue of the inspection apparatus 600 is likely to be limited mainly by the size and acceptance angle of sensor 610, together with cost and complexity of the associated optics. Fortunately, very large CCD arrays with good acceptance angle are available, having tens of megapixels if desired, and measuring several cm2 in area. Compared with the spectrographic technique, therefore, improvements of several orders of magnitude can be expected in throughput and/or sensitivity. The large sensor size and potentially larger NA both contribute to this much larger etendue.

In the simple embodiment of FIG. 6, the filter 612 is required to pass all of the wanted secondary radiation wavelengths $\lambda S1$, $\lambda S2$ etc., and image sensor 610 is also required to be sensitive to radiation at the different wavelengths $\lambda S1$, $\lambda S2$ etc. The embodiments illustrated in FIGS. 9 and 10 and described below include modifications to relax these design constraints. Many variants and further modifications and combinations of these embodiments are possible, as will be apparent to the skilled reader. The embodiments presented here introduce the principles that can be applied by the skilled person to a particular inspection application.

Second Embodiment

Figure 9:
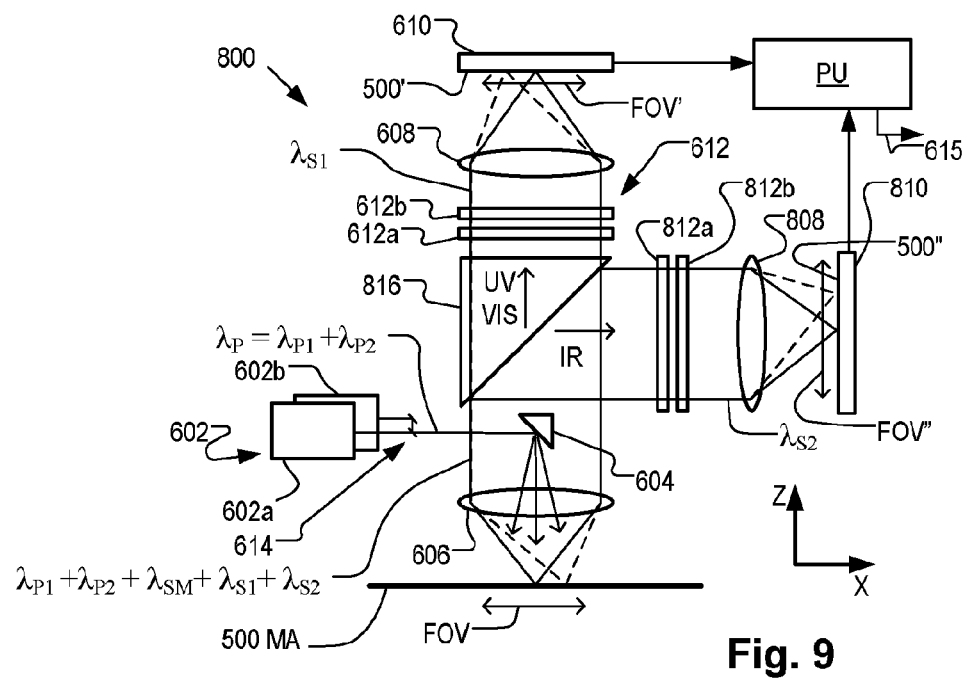
FIG. 9 depicts schematically an apparatus for inspection of an object according to a second embodiment of the present invention.

FIG. 9 is a schematic diagram of an inspection apparatus 800 in a second embodiment of the invention. All the components of the first embodiment inspection apparatus 600 are present and labeled the same as previously, though their characteristics may be modified, for reasons described below. The apparatus 800 is modified by the addition of a second branch in which imaging optics 808, image sensor 810 and filter components 812a and 812b perform similar functions to the components 608, 610, 612a and 612b of the first branch. A dichroic filter 816 is provided at the junction of the two branches, so that the first branch leading to image sensor 610 processes only shorter wavelength radiation (UV and visible, in this example), while the second branch leading to image sensor 810 processes longer wavelengths (infrared). On the second image sensor 810, a second image 500" is formed. For the sake of illustration only, the first branch is shown as imaging rays with the wavelength $\lambda S1$, while the second branch receives and images the reticle using the wavelength $\lambda S2$. As explained already, each of these wavelength labels may represent a single wavelength, or a collection of wavelengths, characteristic of some photo-luminescence or other secondary emission process.

A first advantage of providing two separate branches is that the image sensors 610 and 810 can be chosen according to their performance in respective wavebands, rather than having to find a sensor with adequate performance over the entire spectrum of radiation to be detected. Sensitivity and noise performance of the sensors 610 and 810 in the bands of interest is likely to be better as a result. Similarly, design of the imaging optics 608, 808 will be easier, as it is very costly and difficult to provide imaging optics with low aberration across such a wide spectrum. A third advantage is that the design of filters comprising elements 612a, 612b, 812a, 812b is also relaxed. The number of filter elements in each branch may be reduced, and/or better performance and/or lower cost filters can be provided, within the waveband processed by each branch. Not shown in the diagram, a filter for blocking some or all of the primary radiation wavelengths $\lambda P1$, $\lambda P2$ etc. could be provided between objective lens 606 and the dichroic filter 816, so as to perform its function for both branches in a single component.

Many modifications of the second embodiment are possible, some of which have been mentioned already. In principle, the number of branches is not limited to two. Also, although simultaneous detection using dichroic filter 816 allows the branches to be separated without reducing the throughput of the inspection process, another embodiment could be envisaged in which the branches are switched alternately, by use of a moving mirror or equivalent optical switching element. Alternatively, filters for different wavebands could be switched in and out of the same branch, to take different spectrally-selective images using the same sensor 610 or 810 etc.

Figure 10:
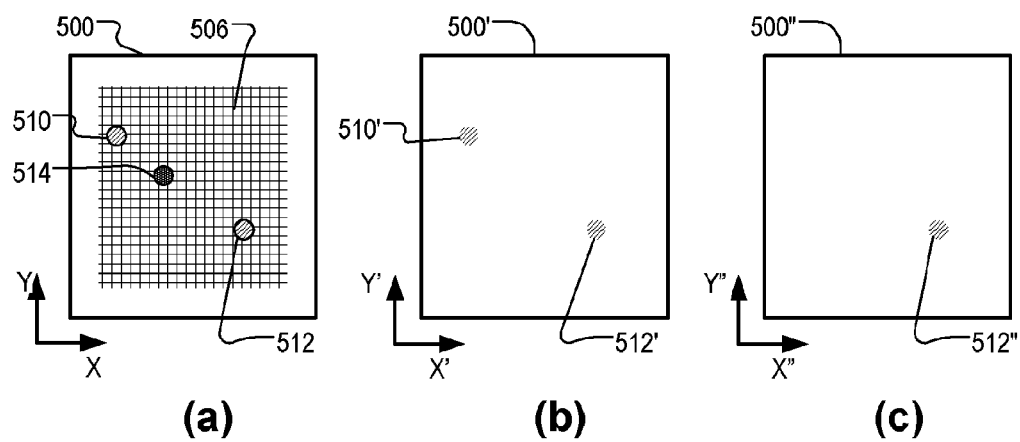
FIG. 10 illustrates (a) the spatial distribution of contaminant particles on an EUV reticle and (b) and (c) two contaminant images obtained using the apparatus of FIG. 9.

FIG. 10 presents in sub-figures (a), (b) and (c) the reticle area 500 and the images 500' and 500" respectively, which are formed on the first branch image sensor 610 and the second branch sensor 810. The image in the first branch (FIG. 10(b)) is assumed to be the same as in the first embodiment (FIG. 7(b)), just for the same of this example. Particles 510 and 512 are detectable in this image as bright spots 510' and 512' respectively. In the image from the second branch sensor 810, the image 500" includes an image 512", corresponding to particle 512, but no image corresponding to particle 510. This indicates that the emission of particle 512 includes secondary radiation at different wavelengths than the image of particle 510. By comparing these different spectrally-selective images, some spectral information is obtained which allows different types, and possibly sizes of particles to be distinguished.

Because each branch has filtering, imaging and sensing components which are more specialized to the particular range of wavelengths contained in that branch, it may also be expected that the sensitivity and signal to noise ratio in each of the images 500' and 500" will be improved compared with the single image 500' in the first embodiment. Smaller particles and/or materials giving weaker signals are therefore more likely to be detected in the second embodiment.

Third Embodiment

Figure 11:
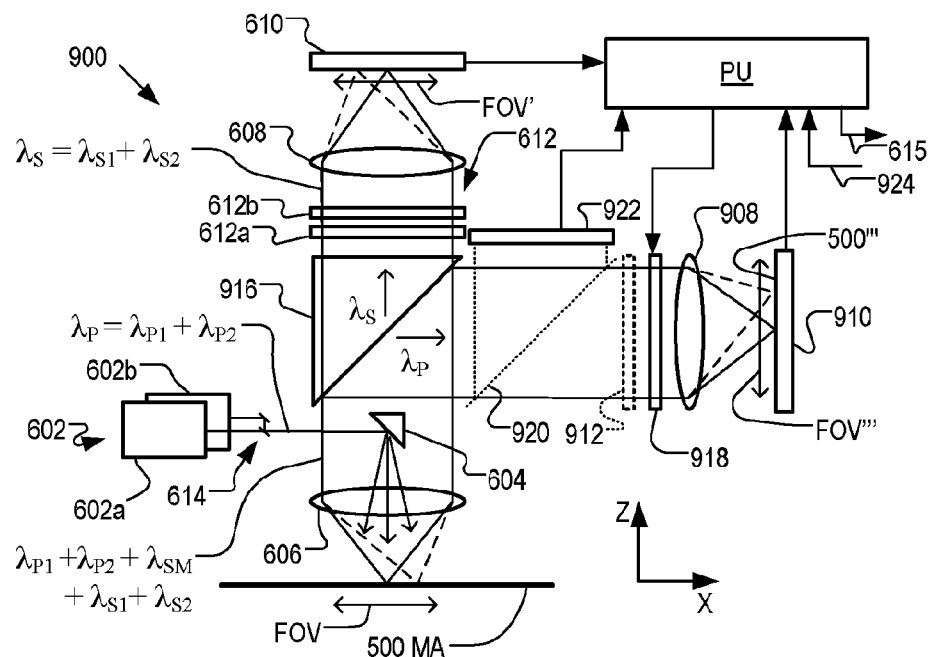
FIG. 11 depicts schematically an apparatus for inspection of an object according to a third embodiment of the present invention.

FIG. 11 illustrates another inspection apparatus 900, which again is based on the apparatus 600, and again is modified to include a second branch. The second branch in this embodiment includes imaging optics 908, image sensor 910 and (optionally) a filter 912. A dichroic mirror 916 is provided to divert scattered primary radiation (wavelength $\lambda P$) into the second branch, where it is focused to form an image 500''' on the sensor 910. A spatial light modulator 918 is provided in the second branch prior to imaging optics 908 and controlled by processing unit PU, with a function that will be described shortly. Filter 912 is optional, since the scattered primary radiation in this example represents the strongest signal and also the wanted signal for imaging on sensor 910. The first branch receives the generally longer wavelengths $\lambda S$ which are characteristic of secondary emission, and forms a spectrally selective image 500' on sensor 610, as in the first embodiment.

More background on the use of Fourier filtering by SLM for reticle inspection can be found in prior patent applications, for example U.S. Pub. 20070258086, the contents of which are incorporated herein by reference. SLM 918 comprises, for example, a liquid crystal (LC) device arranged in an array of pixels, or other addressable segments. SLM 918 is located in an intermediate pupil plane of imaging optics 908, meaning that locations within that plane correspond not to locations within the eventual image 500''', but to spatial frequency components within that image. That is to say, the distribution of radiation intensity in the plane of SLM 918 is a spatial Fourier transform of the image 500''', and the SLM 918 can be referred to also as a Fourier filter. By programming some pixels in the SLM to be opaque and others to be transparent, the contribution of different spatial frequency components to the image 500''' can be controlled. A central group of pixels on an optical axis of the imaging optics will block the zero order scattered radiation, giving a "dark field" image. Blocking other locations across the area of SLM 918 allows patterns of different periodicity to be eliminated from the image also. Many reticle patterns for real semiconductor products include large areas of highly periodic features, representing, for example, bus lines in a microprocessor device, word/bit lines in a memory array and the like, a suitable pattern of opaque pixels can be programmed into SLM 918 so as to block the 1st and higher orders of the diffraction spectrum for these periodicities. This will result in the periodic features being eliminated from the image 500''' which is formed on sensor 910. (In principle, programmable SLM 918 could be replaced by a transparency corresponding to each object (reticle) to be inspected. Needless to say, a SLM 918 which is programmable under software control is likely to be more practical where a large number of different patterning devices or other objects are to be inspected.) It is assumed for this description that SLM is of a transmissive type, but it can equally be of a reflective type, for example an LC device or a micro-mirror array (deformable mirror device DMD).

Figure 12:
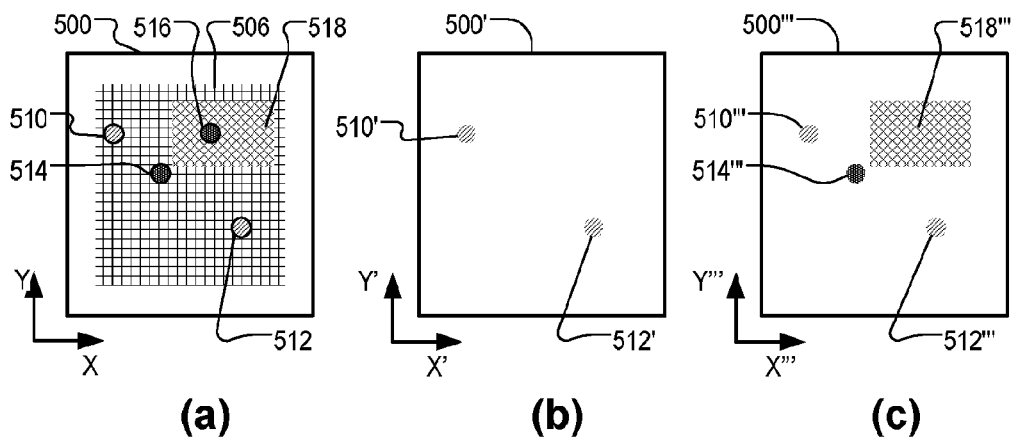
FIG. 12 illustrates (a) the spatial distribution of contaminant particles on an EUV reticle and (b) and (c) two contaminant images obtained using the apparatus of FIG. 11.

FIG. 12 presents at (a) a representation of reticle 500 with various contaminant particles 510, 512, 514 as before, and also a particle 516. Particles 514 and 516 in this example are considered for example metal particles with characteristics very similar to the reticle materials, and therefore difficult to detect in the first and second embodiments which apply only spectrally-selective imaging. The reticle pattern in this example is assumed to be highly periodic across the majority of its area, but with a disrupted (aperiodic (non-periodic) or differently periodic) pattern in an area 518. Particle 516 falls within this disrupted area 518, while particle 514 falls within a highly periodic area.

FIG. 12(b) shows at 500' the spectrally selective image formed on the first branch sensor 610, which for example only is the same as the image 500' in the first embodiment. Particles 510 and 512 can be identified by spots 510' and 512' in this image. Particles 514 and 516 are not visible in this image, because they scatter and/or emit only radiation which is blocked by the filter 612.

FIG. 12(c) represents the image 500''' which is detected by the sensor 910 in the second branch of the apparatus 900, and which exploits the spatial filtering properties of the programmable spatial light modulator. In the dark field image 500''', the areas of the reticle pattern which are highly periodic, with a periodicity corresponding to opaque portions of SLM 918 appear largely blank. In the real image, these blank areas would be the "black" areas, while the other features will represent higher intensity pixels, effectively the negative of what is shown in the drawing. (The same negative representation applies to FIGS. 7 and 9, of course.) Because particle 514 does not have the periodicity of the pattern in the periodic area, a bright spot 514''' appears in the image 500''', allowing this particle to be detected in a way that was not possible in the first and second embodiments. On the other hand, a similar particle 516 which is in the disrupted area 518 is masked by the bright image 518''' of all the pattern features whose periodicity does not correspond to an opaque portion of SLM 918. The correct pattern to apply in SLM 918 can be determined by calculation from the known design of the reticle pattern, from trials made with the apparatus itself, or from measurements of the spatial frequency components made in another apparatus.

Elements 920 and 922 can be provided to generation the Fourier filtering pattern in SLM 918 by a simple adaptive mechanism, rather than needing to know or calculate the appropriate pattern based on the reticle design. At 920, a small part of the scattered light in the intermediate pupil plane is diverted from the main path and directed to a CCD or other image sensor 922, which records the Fourier transform of the scattered radiation, prior to filtering by SLM 918. This signal can be used by unit PU to drive the SLM to suppress the pixels which are brighter than a certain threshold. It may be remembered that the field of view of the inspection apparatus at a given time is a small part of the total reticle area, so that the signals at most times will either be from a portion that has a well-defined periodicity or not. Unit PU is responsible for discriminating between periodic areas and non-period areas, so as to prevent the signals from sensor 910 being interpreted as an indication of contamination, in areas where the reticle pattern is cannot be filtered out. Externally supplied information 924 can be used for this purpose. Information 924 may identify explicitly the areas of the reticle to be excluded, or it may comprise more general information about the pattern, which is then interpreted by unit PU to decide which areas to exclude. Alternatively or in addition, information from the sensor 922 can be analyzed statistically to determine that the area under inspection is not sufficiently periodic to allow contaminant particles to be distinguished reliably.

From this third embodiment, it can be seen that, the use of spatial light modulators and dark field imaging to detect contaminant particles may be useful as an addition to other inspection techniques, even though it is not in itself a complete solution to the problems of reticle inspection, because of its applicability to highly periodic patterns only. The inventors have recognized that the provision of an inspection apparatus which simultaneously applies different techniques increases the chances of detecting contaminant particles, specifically to detect particles that would be missed by those other techniques. Because the two images are taken simultaneously using different subsets of the radiation entering the inspection apparatus, a high measurement throughput can be obtained. Also, increased certainty of particle detection can be obtained by comparing and contrasting the different images 500' and 500''', and different types of contaminant material can be discriminated by the same process. The risk of false detection of contamination by over-sensitive inspection apparatus can be reduced.

With regard to detecting a greater proportion of the contaminant population, it will be appreciated that the dark field imaging technique can detect all types of particle, but only on condition that the underlying pattern is periodic. Spectrally-discriminating imaging techniques (first branch) can detect particles on all types of pattern, but only if a secondary emission is present. Using these techniques in combination, more particles can be detected than by each technique alone. The only limitation is that particles on a non-periodic portion of the pattern can only be detected if a secondary emission is present and detectable by the spectroscopic technique.

Additional Notes

Combined embodiments are possible, having for example the features of both apparatuses 800 and 900, so that three or more images 500', 500" and 500'" can be compared and contrasted both to detect a greater proportion of the total contaminant particle population, and to discriminate more finely between different types of contamination. Information as to the type of contamination present can be useful for example in the choice and control of decontamination (cleaning) process. Information on the type of contamination can also be useful for diagnosing the source of contamination, and taking measures to reduce contamination in future. If enhanced discrimination between contaminant types is required, an option would be to apply the fully spectroscopic techniques described in our prior application to a particular area of interest, identified from the images 500' etc., obtained with the imaging inspection apparatus, 600, 800 or 900. Because the fully spectroscopic technique is only applied in the event that contaminants of interest are detected, it will have less impact on the routine throughput of the inspection process, and hence the lithographic process itself. Radiation can be diverted to a fully spectroscopic instrument by use of a moveable mirror, or the spectroscopic instrument input can be placed at a different location in the inspection apparatus, and the relevant portion of the reticle or other object to be inspected can be placed under it, in the direction of the processing unit PU, referring to the location of the contaminant particle in one or more of the detected images 500' etc.

As an example, the primary radiation wavelength $\lambda P$ may be UV radiation with a wavelength 266 nm. Scattered and emitted radiation, including the primary radiation, but also now secondary radiation by photoluminescence/Raman emission, is collected by the apparatus, for example apparatus 900 in the third embodiment. The secondary radiation which will have a wavelength longer than 266 nm is filtered in the first branch of the apparatus to remove the primary radiation and also a secondary radiation $\lambda SM$ from the reticle itself. In the case of apparatus 900 and similar embodiments, the primary radiation is directed through a Fourier filter formed by a spatial light modulator to remove periodic components of the reticle pattern, to obtain a dark field image in which contaminant particles present on periodic areas of the reticle will be distinguished.

Multiple excitation wavelengths $\lambda P1$, $\lambda P2$ etc. can be used, for example, 266, 355 and 532 nm, which are the YAG laser 4th, 3rd and 2nd harmonics, to improve excitation efficiency of different particle materials. In this case, additional spectral notch filters can be added in the same imaging branch to remove to the scattered light at 355 and 532 nm, as well as 266 nm. Alternatively, additional dichroic mirrors can be used with multiple imaging branches, allowing multiple dark field images and/or photoluminescence images to be recorded. In other words, dark field images at individual wavelengths 266, 355 and 532 nm can be recorded simultaneously, as well as images of secondary radiation in the ranges 266-355, 355-532 and 532 and above. This large number of independent images, can be obtained simultaneously, but allows correlation between data to identify materials based on their spectral signature, and also to further increase detection efficiency and reduce false alarms.

The selection of wavelengths is a matter for experiment, to optimize detection of contaminant particles, including the ability discriminate contaminant materials from the reticle material and the primary radiation. As a starting point for such experimentation, it is known that most organic materials will be excited by the UV wavelengths such as 266 nm. 355 nm is useful for Aluminum—present as oxide. 532 nm is useful for Raman emission and certain organics.

Application to Lithography

Figure 13:
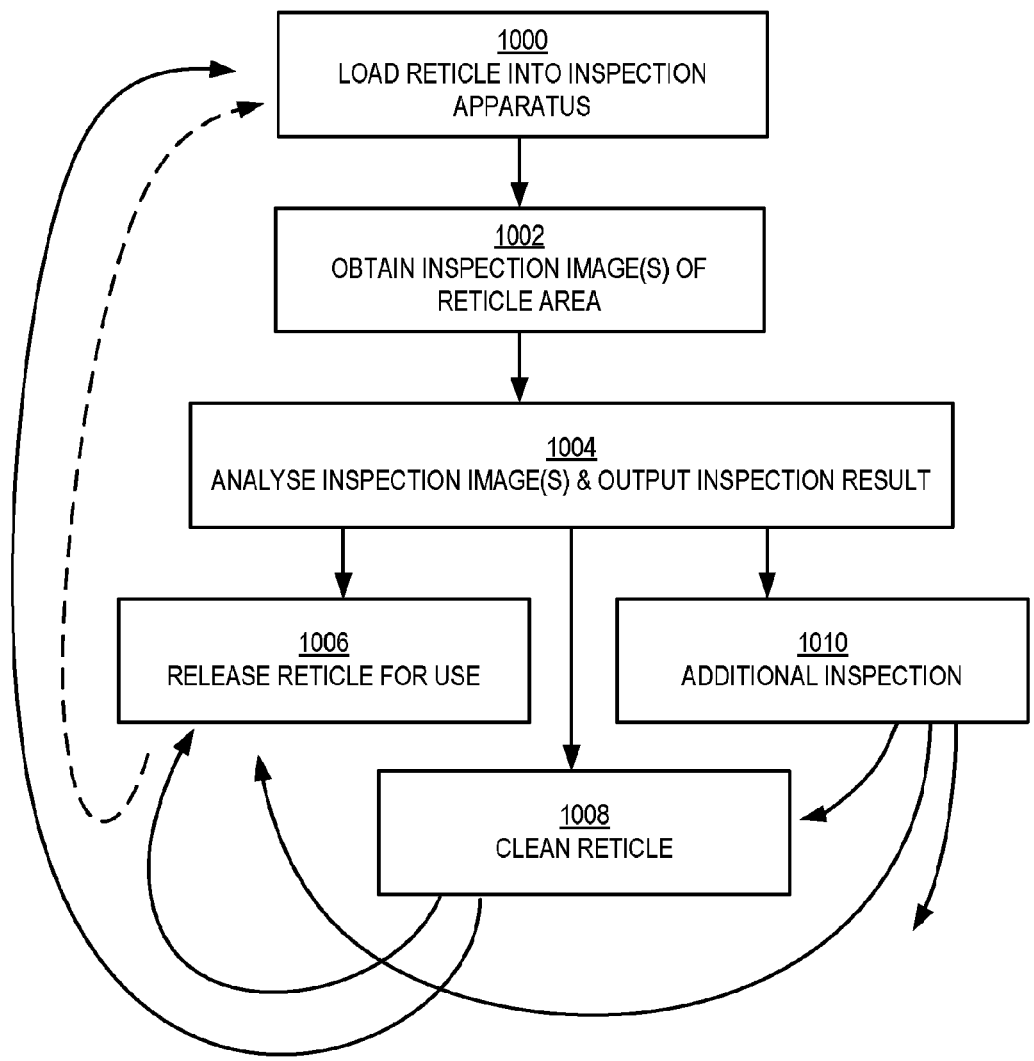
FIG. 13 is a flowchart of an inspection process applied to reticles in a lithography process.

FIG. 13 shows the main process steps of an inspection regime applied to reticles in a EUV lithography process, using lithography apparatus such as those shown in FIGS. 1-4. The process can be adapted to inspection of reticles and other patterning devices in other types of lithography, as well as to the inspection of objects other than lithography patterning devices.

Inspection apparatus, such as the apparatus 600, 800 or 900 of the embodiments described above, may be integrated within the reticle housing of the lithographic apparatus, so that the reticle under inspection is mounted on the same support structure (mask table) MT used during lithographic operations. The mask table may be moved under the inspection apparatus, or equivalently the inspection apparatus is moved to where the reticle is already loaded. Alternatively, reticle 500 may be removed from the immediate vicinity of support structure MT to a separate inspection chamber where the inspection apparatus is located. This latter option avoids crowding the lithographic apparatus with additional equipment, and also permits the use of processes that would not be permitted or would be undesirable to perform within the lithographic apparatus itself. The inspection chamber can be closely coupled to the lithographic apparatus, or quite separate from it, according to preference. Alternative inspection apparatuses can be included in the same or a different chamber, to allow the detection of different types of particles by different processes.

Returning to FIG. 13, reticle 500 which is an example of a patterning device used in the lithographic apparatus is loaded at step 1000 into the inspection apparatus (or the inspection apparatus is brought to where the reticle is already loaded). Prior to inspection, the reticle may or may not have been used in the lithographic process. Using the inspection apparatus 600 etc., one or more images of the vertical are obtained at step 1002. As mentioned already, these may be a single image of the entire reticle area, or a set of sub-area images which are processed individually or stitched into a larger image. The images obtained may be differently filtered images for detecting one or more wavebands of secondary radiation, and/or a dark field image using primary radiation scattered by the reticle. Using the apparatus 800, 900 and variants thereof, these different images can be obtained simultaneously without affecting throughput of the inspection.

At 1004, processing unit PU or an external computer analyses the inspection images individually and in combination, to make decisions about further processing of the reticle. If the reticle is found to be clean, it is released at step 1006 for use in the lithographic process. As indicated by the broken arrow, the reticle will return for inspection at a later time, after a period of operation. If the analysis at 1004 indicates that cleaning of the reticle is required, a cleaning process is initiated at 1008. After this cleaning process the reticle may be released automatically for re-use, or returned for inspection to confirm success of the cleaning. A third potential outcome of the analysis at step 1004 is to instruct additional inspection. As mentioned above, for example, inspection using a fully spectroscopic apparatus may be desired. Alternatively, if the reticle is found to be dirty it may be taken out of the litho tool and inspected more thoroughly using other tools, e.g., SEM (scanning electron microscopy. This may be to discriminate between different sizes of particles and/or different material types, either for diagnosis of problems in the area of lithographic apparatus or to decide, in fact, the reticle can be released for use. It should be noted that, because different materials may exhibit different qualities and strengths of secondary emission, the contaminant particle which appears brighter than another particle in one of the spectroscopic images 500', 500" etc. may in fact be physically smaller than a particle which appears not so bright. A decision might be made that a particle which is detected in the images is in fact small enough, or in such a position, as to create no problem in the lithographic process.

Embodiments of the methods and apparatus of the disclosure also allow the detection of a particle on a patterned reticle without the necessity of resolving the pattern itself and without comparing the signal to a reference signal. This allows the inspection of "single die" reticles because a complicated die-to-database inspection is not required. In addition, avoiding comparison of two reference objects avoids the associated image alignment issues.

Embodiments of the methods and apparatus of the present disclosure can in principle be used for the inspection of any type of pattern or mask, or indeed any object, not just an EUV lithographic patterning device. The method can also be used to detect smaller particles which are, for example, less than 100 nanometers, less than 50 nanometers or even less than 20 nanometers, and can be used for detection of all these on the patterned side of substrates such as EUV reticles. The optical system which collects and detects the secondary radiation emitted by the contaminant material need not have the power to resolve the individual particles. The presence of the radiation at the secondary radiation wavelength is sufficient evidence of the contamination in a given area.

As mentioned already the inspection apparatus 600, 800 or 900 can be provided as an in-tool device, that is, within a lithographic system, or as a separate apparatus. As a separate apparatus, it can be used for purposes of reticle inspection (e.g., prior to shipping). As an in-tool device, it can perform a quick inspection of a reticle prior to using the reticle for a lithographic process. It may in particular be useful to perform inspections in between the lithographic processes, for example to check after every N exposures whether the reticle is still clean.

Processing of signals from the sensor may be implemented by processing unit PU in hardware, firmware, software, or any combination thereof. Unit PU may be the same as a control unit of the lithographic apparatus, or a separate unit, or a combination of the two. Embodiments of the invention of various component parts of the invention may also be implemented as instructions stored on a machine-readable medium, which may be read and executed by one or more processors. A machine-readable medium may include any mechanism for storing or transmitting information in a form readable by a machine (e.g., a computing device). For example, a machine-readable medium may include read only memory (ROM); random access memory (RAM); magnetic disk storage media; optical storage media; flash memory devices; electrical, optical, acoustical or other forms of propagated signals (e.g., carrier waves, infrared signals, digital signals, etc.), and others. Further, firmware, software, routines or instructions may be described herein as performing certain actions. However, it should be appreciated that such descriptions are merely for convenience and that such actions in fact result from computing devices, processors, controllers, or other devices executing the firmware, software, routines, instructions, etc.

It is to be appreciated that the Detailed Description section, and not the Summary and Abstract sections, is intended to be used to interpret the claims. The Summary and Abstract sections may set forth one or more but not all exemplary embodiments of the present invention as contemplated by the inventor(s), and thus, are not intended to limit the present invention and the appended claims in any way.

The present invention has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

What is claimed is:

1. A method comprising:
   directing primary radiation at one or more first wavelengths, from a radiation source, to interact with an article to produce secondary radiation, the secondary radiation being produced from the primary radiation interacting with non-fluorescent material of a contaminant particle on the article, the secondary radiation having one or more second wavelengths different than the one or more first wavelengths;
   forming an image, with detection optics, of the article based on filtering out, using a filter, the primary radiation and transmitting, using the filter, the secondary radiation; and
   detecting the image with an image sensor.

2. The method of claim 1, further comprising:
   detecting the presence and location of the contamination particles with a processing unit for processing of a signal from the imaging sensor.

3. The method of claim 1, wherein the primary radiation is at a plurality of distinct first wavelengths, and
   wherein the filter has a spectral response which includes a plurality of distinct stop bands corresponding to at least two of the distinct first wavelengths.

4. The method of claim 1, comprising operating a plurality of branches in parallel, each branch forming an image of the illuminated article, detecting the image, and using secondary radiation of a different wavelength or wavelengths selected from the one or more second wavelengths.

5. The method of claim 4, further comprising analyzing at least two images detected in different branches to detect the presence and location of the contamination particles.

6. The method of claim 5, wherein the presence of the contamination particles is detected based on the location of image features detected in at least one of the images.

7. The method of claim 1, wherein at least a portion of the filtered out primary radiation is diverted into a dark field imaging system having a spatial filter in an intermediate pupil plane to form and detect a dark field image of the article under inspection.

8. The method of claim 7, wherein:
the spatial filter is arranged to block a selected spatial frequency component, and
the spatial frequency component is selected based on the article under inspection.

9. The method of claim 1, wherein the first and second wavelengths are selected to detect contaminant particles of metal oxide material.

10. The method of claim 1, wherein the first and second wavelengths are selected to detect contaminant particles of organic material.

11. The method of claim 1, wherein the first and second wavelengths are selected to detect contaminant particles of non-noble metals.

12. A method of manufacturing a device, comprising:
inspecting an article for any contamination on the article, wherein the article is used to transfer a pattern from the article to the device,
wherein the inspecting comprises:
directing primary radiation at one or more first wavelengths from a radiation source, to interact with the article to produce secondary radiation, the secondary radiation being produced from the primary radiation interacting with non-fluorescent material of a contaminant particle on the article, the secondary radiation having one or more second wavelengths different than the one or more first wavelengths;
forming an image, with detection optics, of the article by filtering out, using a filter, the primary radiation and transmitting, using the filter, the secondary radiation; and
detecting the image with an image sensor.

13. An inspection apparatus for inspecting an article to detect and locate contaminant particles, the apparatus comprising:
a radiation source configured to generate primary radiation at one or more first wavelengths;
illumination optics arranged to receive the primary radiation and to illuminate at least a portion of the article with the primary radiation; and
an imaging optical system comprising:
detection optics arranged to form an image of the illuminated article, and
an image sensor arranged to detect the image of the illuminated article,
wherein the detection optics comprise a filter configured to remove the primary radiation from the detected image, so that the detected image is formed using secondary radiation at one or more second wavelengths different from the first wavelengths, said secondary radiation being produced from the primary radiation interacting with non-fluorescent material of the contaminant particles.

14. The apparatus of claim 13, further comprising a processing unit for processing of a signal from the imaging sensor, thereby to detect the presence and location of the contamination particles.

15. The apparatus of claim 13, wherein the radiation source is arranged to generate the primary radiation at a plurality of distinct first wavelengths, and
wherein the filter has a spectral response which includes a plurality of distinct stop bands corresponding to at least two of the distinct first wavelengths in the primary radiation.

16. The apparatus of claim 13, wherein the imaging optical system comprises a plurality of branches operating in parallel, each branch forming and detecting an image from the secondary radiation at a different wavelength or wavelengths selected from the one or more second wavelengths.

17. The apparatus of claim 16, comprising a processing unit arranged to process signals from at least two imaging sensors, each of the imaging sensors in a different branch, thereby to detect the presence and location of the contamination particles.

18. The apparatus of claim 13, further comprising a dark field imaging optical system having a spatial filter in an intermediate pupil plane, thereby to form and detect a dark field image from at least a portion of the filtered out primary radiation.

19. The apparatus of claim 18, wherein the spatial filter is a programmable spatial light modulator, said programmable spatial light modulator adjustable to block different spatial frequency components when inspecting different articles.

20. A lithographic apparatus comprising:
a support configured to support an article;
a support configured to support a substrate;
a projection optical system configured to transfer a pattern from the article to the substrate; and
an inspection apparatus configured to inspect an article to detect and locate contaminant particles, the apparatus comprising:
a radiation source configured to generate primary radiation at one or more first wavelengths;
illumination optics arranged to receive the primary radiation and to illuminate at least a portion of the article with the primary radiation;
an imaging optical system comprising:
detection optics arranged to form an image of the illuminated article, and
an image sensor arranged to detect the image of the illuminated article,
wherein the detection optics comprise a filter configured to remove the primary radiation from the detected image, so that the detected image is formed using secondary radiation at one or more second wavelengths different from the first wavelengths, said secondary radiation being produced from the primary radiation interacting with non-fluorescent material of the contaminant particles,
wherein the inspection apparatus is operable to inspect the article without removing said article from the lithographic apparatus.

* * * * *